United States Patent
Park et al.

(10) Patent No.: US 8,790,927 B2
(45) Date of Patent: Jul. 29, 2014

(54) **ANTICANCER METHOD COMPRISING PLANT STEM CELL LINE DERIVED FROM *TAXUS* CAMBIUM OR PROCAMBIUM**

(71) Applicant: Unhwa Corporation, Jeollabuk-Do (KR)

(72) Inventors: Joong Hyun Park, Jeollabuk-Do (KR); Min Jung Lim, Jeollabuk-Do (KR); Il Seok Oh, Iksan (KR); Dae Hee Lee, Jeollabuk-Do (KR); Jung Chang Lee, Jeollabuk-Do (KR); Eun Kyong Lee, Iksan (KR); Young Woo Jin, Jeollabuk-Do (KR)

(73) Assignee: Unhwa Corporation, Jeollabuk-Do (KR)

( * ) Notice: Subject to any disclaimer, the term of this patent is extended or adjusted under 35 U.S.C. 154(b) by 0 days.

(21) Appl. No.: 13/755,517

(22) Filed: Jan. 31, 2013

(65) Prior Publication Data

US 2013/0315877 A1   Nov. 28, 2013

Related U.S. Application Data

(63) Continuation of application No. 12/682,574, filed as application No. PCT/KR2008/006002 on Oct. 10, 2008, now abandoned.

(30) Foreign Application Priority Data

Oct. 10, 2007   (KR) .................. 10-2007-0102178

(51) Int. Cl.
*C12N 5/00* (2006.01)
*C12N 5/02* (2006.01)

(52) U.S. Cl.
USPC ........................................ 435/422; 435/410

(58) Field of Classification Search
USPC ................................. 435/410, 422
See application file for complete search history.

(56) References Cited

U.S. PATENT DOCUMENTS

| 5,310,672 A | * | 5/1994 | Wann et al. | ............ 435/123 |
| 5,407,816 A | * | 4/1995 | Bringi et al. | ............ 435/123 |
| 5,850,032 A |   | 12/1998 | Wann |   |
| 7,264,951 B1 | * | 9/2007 | Bringi et al. | ............ 435/123 |

FOREIGN PATENT DOCUMENTS

| KR | 10 1995 0005081 |   | 5/1995 |
| KR | 10 2004 0108052 A | | 12/2004 |
| WO | 2007052876 A1 |   | 5/2007 |

OTHER PUBLICATIONS

Khosroushahi et al. "Improved Taxol production by combination of inducing factors in suspension cell culture of *Taxus baccata*," Cell Biology International, 30; (2006), pp. 262-269.*
Mekhail, et al., Paclitaxel in cancer therapy, Expert Opin. Pharmacother., 3(6):755-766 (2002).
Khoroushahi, A. Yari, et al., Improved Taxol Production by combination of inducing factors in suspension cell culture of *Taxus baccata*, Cell Biology International, 30:262-269 (2006).

* cited by examiner

*Primary Examiner* — Susan McCormick Ewoldt
(74) *Attorney, Agent, or Firm* — Tristan A. Fuierer; Andrew D. Gerschutz; Moore & Van Allen, PLLC

(57) ABSTRACT

The present invention relates to a composition for preventing or treating cancer, which contains, as an active ingredient, a *Taxus* cambium- or procambium-derived cell line; a lysate thereof; an extract thereof; or a culture medium thereof. The cell line, the lysate, the extract, and the culture medium has minimized side effects compared to the conventional therapeutic drugs, is safe to the human body, is involved directly in the growth of cancer to induce cancer cell death, and shows anticancer activity of inhibiting angiogenesis occurring in carcinogenesis. Accordingly, the cell line, the lysate, the extract and the culture medium is useful for the prevention, treatment and alleviation of cancer.

10 Claims, 13 Drawing Sheets (d) De-differentiated cells

Primary phloem

Cortex

Epidermis

Procambium

Tumor volume (mm³) = a × b² × 0.4
a: the longest diameter
b: the shoetest diameter Caki (renal cancer)

extract concentration

HepG2 (liver cancer)

extract concentration

ANTICANCER METHOD COMPRISING PLANT STEM CELL LINE DERIVED FROM *TAXUS* CAMBIUM OR PROCAMBIUM

CROSS-REFERENCE TO RELATED APPLICATIONS

This application is a continuation of U.S. patent application Ser. No. 12/682,574, now abandoned, filed on Apr. 9, 2010, entitled "ANTICANCER COMPOSITION COMPRISING PLANT STEM CELL LINE DERIVED FROM *TAXUS* CAMBIUM OR PROCAMBIUM" in the name of Joong Hyun Park, et al., which claims the benefit of International Patent Application No. PCT/KR2008/006002, filed on Oct. 10, 2010, which also claims the benefit of Korean Patent Application No. KR 10-2007-0102178, filed on Oct. 10, 2007, all of which are hereby incorporated by reference herein in their entirety.

TECHNICAL FIELD

The present invention relates to a composition for preventing or treating cancer, which contains, as an active ingredient, a *Taxus* cambium- or procambium-derived cell line; a lysate thereof; an extract thereof; or a culture medium thereof.

BACKGROUND ART

Apoptosis is an active process of cell death that occurs through the regulation of various gene expressions and protein activities in cells according to programmed signals. Apoptosomes formed through this process are removed by the action of phagocytes such as the surrounding cells or as macrophages, such that they do not cause inflammation. Such apoptosis is frequently observed in various normal physiological processes of living organisms and known to be deeply involved in the process of development of various diseases. Namely, the development of abnormal apoptosis can lead to neurodegenerative disorders, immune disorders and cardiovascular diseases, and the abnormal inhibition of apoptosis can cause cancer.

More specific examples of diseases which are caused by the abnormal development and inhibition of apoptosis include cancers induced by the abnormal expression of genes such as p53, p16 and Bcl-2, infections with HIV Herpes and influenza virus, and autoimmune diseases such as type 1 diabetes, rheumatoid arthritis, multiple sclerosis and myasthenia gravis. The apoptosis of cells of an individual is a general mechanism for removing abnormal cells, that is, unrecoverable genetically damaged cells, from the individual in order to prevent the development of tumors caused by either the genetically damaged cells or the induction of inappropriate differentiation by differentiation stimuli. This concept is supported by the fact that general anticancer agents induce the death of cancer cells through an apoptosis process associated with the inhibition of proliferation of cancer cells (Barry, M. A. et al., *Biochem Pharmacol.*, 40:2353, 1990; Hickman, J. A., *Cancer Metastasis Rev.*, 11:121, 1992).

Accordingly, the disturbance of apoptosis process induces the survival of damaged cells and cells that started to be damaged and the growth of these cells, and thus the inhibition of apoptosis plays an important role in a carcinogenic process. In addition, it has been reported that substances having cancer preventive effects induce the apoptosis of such abnormal cells and that the induction of apoptosis by these substances is associated at least with the cancer preventive activity thereof (Fesus, L., *J. Cell Biochem.*, 22:151, 1995; Reddy, B. S., *Cancer Res.*, 57:420, 1997)

Meanwhile, enormous research expenses have been paid for studies on the mechanism of development and treatment of cancers, but cancers still remain as incurable diseases, and various cancer therapies cause side effects (Goodman et al., *Cancer Res.*, 9:2295, 1987). Accordingly, many efforts have been made to study and develop novel drugs and formulations for inhibiting cancers, and particularly, studies on the development of anticancer substances from natural materials having small side effects have been drawing interest.

Some of the present inventors developed a method for providing cambium- or procambium-derived cell lines which overcome the problem of variation caused by dedifferentiation, can stably proliferate and has high genetic stability, and found that, when a *Taxus*-derived cell line among the cell lines is cultured, paclitaxel is obtained at a high yield (PCT/KR2006/001544). However, the anticancer effects of a *Taxus* cambium- or procambium-derived cell line itself have not yet been reported.

Accordingly, the present inventors have made extensive efforts to develop a natural material-derived anticancer composition, which has minimized side effects compared to the conventional anticancer agents and shows excellent anticancer activity, and, as a result, have found that a *Taxus* cambium- or procambium-derived homogeneous cell line; a lysate thereof, an, extract thereof; or culture thereof shows cancer cell-killing activity, thereby completing the present invention.

SUMMARY OF INVENTION

It is an object of the present invention to provide a natural material-derived composition, which has minimized side effects compared to prior anticancer agents and shows activity for preventing and treating cancer.

To achieve the above object, in one aspect, the present invention provides a pharmaceutical composition for preventing or treating cancer, which contains any one or more selected from the group consisting of a cell line, which is derived from the cambium or procambium of *Taxus* and has the following characteristics; a lysate thereof; an extract thereof; and a culture thereof:

(a) it is morphologically characterized by a large number of vacuoles;

(b) it is in an innately undifferentiated state; and (c) it is a homogeneous cell line.

In another aspect, the present invention provides a functional food for preventing or improving cancer, which contains any one or more selected from the group consisting of said cell line; said lysate; said extract; and said culture.

In still another aspect, the present invention provides the use of any one among said cell line, said lysate; said extract; and said culture to prevent or treat cancer.

In yet another aspect, the present invention provides a method for preventing or treating cancer, the method comprises using any one or more selected from the group consisting of said cell line; said lysate; said extract and said culture.

Other features and aspects of the present invention will be apparent from the following detailed description and the appended claims.

BRIEF DESCRIPTION OF DRAWINGS

FIG. 2(c) shows the PDA spectrum of the paclitaxel standard.

DETAILED DESCRIPTION OF THE INVENTION AND PREFERRED EMBODIMENTS

Figure 1:
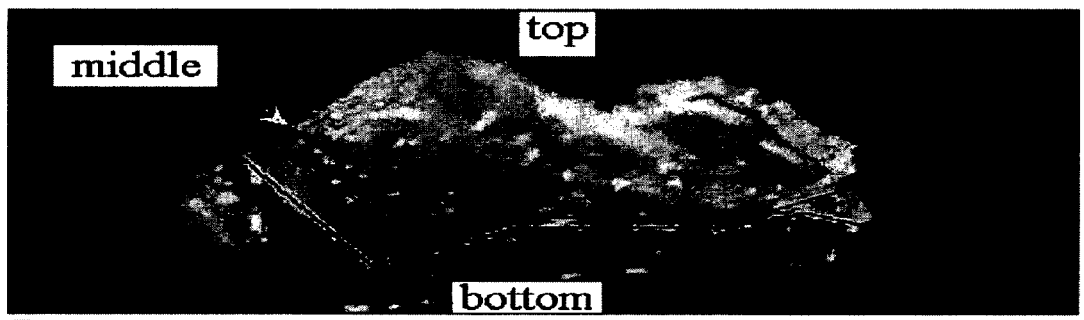
FIG. 1(a) illustrates the division of cells from procambium and cambium at 4-7 days of initial culture whereby the top indicates a tissue containing phloem, cortex and epidermis, the middle indicates cambium, the bottom indicates xylem, and an arrow head indicating the separation between the cambium layer and the tissue containing phloem, cortex and epidermis.
In FIG. 1(b), "A" indicates a phloem/cortex/epidermis-containing tissue-derived cell line, "B" indicates a cambium-derived cell line, and "C" indicates xylem in which cell division did not occur.
In FIG. 1(c), "A" shows the twig observed after 30 days of culture as described herein, "B" is a photograph after 35 days of culture as described herein, and "C" is a photograph after 40 days of culture as described herein.
FIG. 1(d) illustrates that the cell lines were morphologically characterized by a large number of vacuoles and were in an undifferentiated state.
Figure 1:
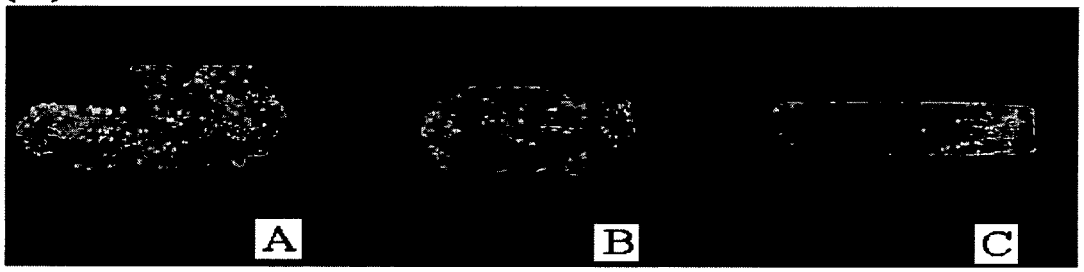
Figure 1:
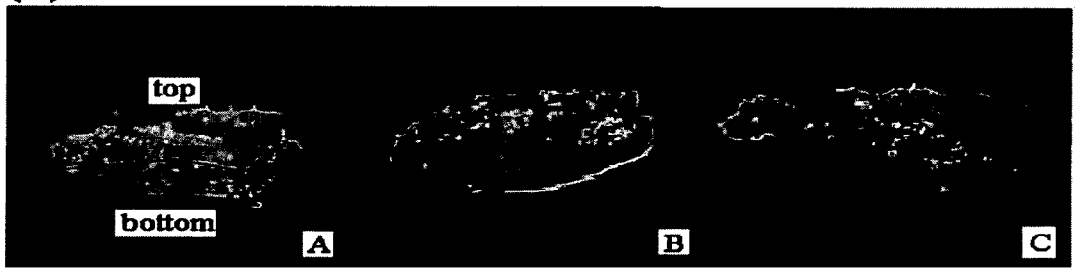
Figure 1:
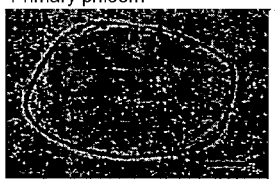
Figure 1:
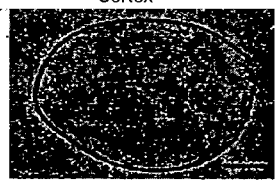
Figure 1:
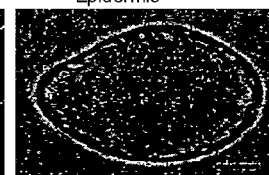
Figure 1:
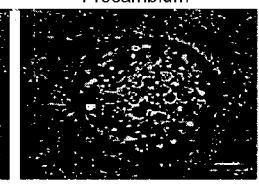

Unless otherwise defined, all technical and scientific terms used herein have the same meaning as commonly understood by one of ordinary skill in the art. Generally, the definitions of various terms used herein are well known and conventionally used in the art.

The definition of main terms used in the detailed description of the invention is as follows. As used herein, the term "cambium" refers to a tissue that thickens the stem and root to allow the plant grow volumetrically. It was reported that when the cambium, a meristem where the most active cell division occurs, is used as an explant for plant tissue culture, rapid and mass production of cells is possible (Korean Patent 10-0533120).

As used herein, the term "procambium" refers to a primary meristem derived from an initial cell group, and the cambium that is a primary meristem is derived from the procambium without the intervene of permanent tissue.

As used herein, the term "lysate" refers to a cell lysate obtained by disrupting cells through a chemical method with, for example, a detergent, or a physical method. The term "extract" of a cell line refers to a substance obtained by dissolving cells in a solvent and isolating the cells, and the extract can be concentrated through distillation or evaporation.

As used herein, the term "innately undifferentiated" means that cells are not present in an undifferentiated state through a dedifferentiation process, but are originally maintained in a pre-differentiated state.

In one aspect, the present invention relates to a pharmaceutical composition for preventing or treating cancer, which contains any one or more selected from the group consisting of a cell line which is derived from the cambium or procambium of *Taxus*; a lysate thereof; an extract thereof; and a culture thereof:

The *Taxus* cambium- or procambium-derived cell line according to the present invention has the following characteristics:
(a) it is morphologically characterized by a large number of vacuoles;
(b) it is in an innately undifferentiated state; and
(c) it is a homogeneous cell line.

The *Taxus* cambium- or procambium-derived cell line according to the present invention is additionally characterized in that: (a) it is present as single cells during suspension culture; (b) it has a higher growth rate than those of cell lines derived from tissues other than the cambium or procambium of *Taxus* and is cultured stably; and (c) it has low sensitivity to shear stress in a bioreactor compared to cell lines derived from tissues other than the cambium or procambium of *Taxus*.

The cell line according to the present invention is preferably obtained using an isolation method comprising the following steps of:
(a) obtaining a *Taxus* cambium- or procambium-containing tissue;
(b) inducing a cambium or procambium layer proliferated from the cambium or procambium and an amorphous callus layer proliferated from tissues other than the cambium or procambium by culturing the obtained *Taxus* cambium- or procambium-containing tissue; and
(c) collecting a cell line from the cambium or procambium layer.

In the isolation method, step (c) is preferably performed by proliferating the tissue in a medium, which contains 3-5 wt % of raw sugar or sugar and at least one substance selected from the group consisting of methyl jasmonate, fungal extract, bacterial extract, yeast extract, chitosan, glucomanan, glucan, phenylalanine, benzoic acid, salicylic acid, arachonic acid, STS, mevalonalonate N-benzolyglycine, ABA, SNP, IPP, BHT, CCC, ethephon, hippuic acid, ammonium ceric nitrate, $AgNO_3$, vanadyl sulfate, p-aminobenzoic acid, brassinosteroids, sodium alginate, and sodium acetate, and then collecting the proliferated cell line. Herein, methyl jasmonate is preferably contained in an amount of 10-100 µM.

The medium used in the present invention is a conventional medium for plant tissue culture, and examples thereof include, but are not limited to, N6 medium, SH medium, MS medium, AA medium, LS medium, B5 medium, WPM medium, LP medium, White medium, GD medium, DKW medium, DCR medium, etc.

In the present invention, the extract is preferably obtained using a solvent selected from the group consisting of distilled water, alcohol, acetone, DMSO (dimethyl sulfoxide), and mixed solvents thereof.

In one Example of the present invention, it was found that the *Taxus* cambium-derived cell line and procambium-derived cell line of the present invention had the effect of inhibiting reactive oxygen species induced by $H_2O_2$, suggesting that they had an antioxidant effect. Because reactive oxygen species (ROS) produced in vivo cause cell mutations by binding to cellular molecules, such as intracellular DNA, proteins and lipids, and are involved in cancer tissue formation by inhibiting the normal function of cells, it can be seen that the cell lines of the present invention have the effect of preventing cancer.

In another Example of the present invention, the *Taxus* cambium-derived cell line and procambium-derived cell line of the present invention were administered to mice, and then cancer tissues resected from the mice were observed. As a result, it was shown that the *Taxus* cambium-derived cell line and procambium-derived cell line of the present invention inhibited the growth of cancer tissues, inhibited angiogenesis as one of anticancer mechanisms, and enhanced the infiltration of immune cells into cancer tissue.

In still another Example of the present invention, colon cancer, oral cavity carcinoma, lung cancer, prostate cancer, osteosarcoma, leukemia, uterine cancer, skin cancer, pancreas cancer, breast cancer, gastric cancer, renal cancer and liver cancer cell lines were treated with each of a distilled water extract, methanol extract and acetone extract of the cell lines in order to examine effects of the extracts on cancer cell death. As a result, it was shown that the cell line extracts according to the present invention were effective for the prevention and treatment of, but not limited to, colon cancer, oral cavity carcinoma, lung cancer, prostate cancer, osteosarcoma, leukemia, uterine cancer, skin cancer, pancreas cancer, breast cancer, gastric cancer, renal cancer and liver cancer.

Accordingly, it was found as described above that the cell lines and extracts thereof had activity for preventing and treating cancer. Thus, even though in the present invention, there is no specific example showing that a composition containing a lysate or culture of the cell line shows the effect of preventing and treating cancer, it will be obvious to those skilled in the art that the composition containing the lysate or culture of the cell line according to the present invention can also show the effect of preventing and treating cancer.

In still another Example of the present invention, existence of paclitaxel in the cell line of present invention was analyzed. When the cell line according to the present invention is cultured in a medium containing an elicitor, it can produce paclitaxel at a high concentration. The inventive cell line, which has not been cultured in conditions allowing the production of paclitaxel or has been treated under specific conditions so as not to produce paclitaxel, was tested to examine whether it contains paclitaxel, and LC data were analyzed. As a result, it was shown that the cell line contained no paclitaxel. Thus, it is thought that the anticancer activity of the cell line of the present invention is not the action of paclitaxel known to be produced from *Taxus*, but is the anticancer activity of the cell line itself. In addition, because the cell line according to the present invention shows anticancer effects even when it is orally administered, the anticancer effect of the inventive cell line does not seem to be the action of paclitaxel which is used as an injection solution, because paclitaxel is ineffective when it is orally administered.

A composition for preventing or treating cancer, containing any one or more of the cell line according to the present invention; a lysate thereof an extract thereof; and culture thereof, may be provided as a pharmaceutical composition containing any one or more selected from the group consisting of the cell line; the lysate thereof, the extract thereof; and the culture thereof alone or in combination with at least one pharmaceutically acceptable carrier, excipient or diluent. The cell line, the lysate, the extract, or the culture of the cell line may be contained as pharmaceutical composition in a pharmaceutically effective amount depending on disease and its severity, the patient's age, weight, health condition and sex, the route of administration and the period of treatment.

As used herein, the term "pharmaceutically acceptable composition" refers to a composition that is physiologically acceptable and does not cause gastric disorder, allergic reactions such as vertigo, or similar reactions, when administered to humans.

Examples of said carrier, excipient or diluent may include lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinylpyrrolidone, water, methylhydroxybenzoate, propylhydroxybenzoate, talc, magnesium stearate and mineral oils.

The pharmaceutical composition may additionally contain fillers, anti-aggregating agents, lubricants, wetting agents, perfumes, emulsifiers and preservatives. Also, the pharmaceutical composition of the present invention may be formulated using a method well known in the art, such that it can provide the rapid, sustained or delayed release of the active ingredient after administration to mammals. The formulation may be in the form of powders, granules, tablets, emulsions, syrups, aerosols, soft or hard gelatin capsules, sterile injection solutions, sterile powders, etc.

In another aspect, the present invention provides a functional food for preventing or improving cancer, which contains any one or more selected from the group consisting of said cell line; said lysate, said extract; and said culture derived from the cambium or procambium of *Taxus*.

As used herein, the term "functional food" refers to a food, the functionality of which has been improved by adding the cell line according to the present invention, the lysate, the extract, or the culture of the cell line thereto. For example, the anticancer effect of the cell line of the present invention or the cell line extract may be used to prepare a functional food for preventing and alleviating cancer.

The functional food of the present invention may contain various nutrients, vitamins, minerals (electrolytes), flavoring agents such as synthetic flavoring agents and natural flavoring agents, coloring agents, fillers, peptic acid and its salt, alginic acid and its salt, organic acids, protective colloid thickeners, pH regulating agents, stabilizers, preservatives, glycerin, alcohol, carbonizing agents that are used in carbonated beverages.

EXAMPLES

Hereinafter, the present invention will be described in further detail with reference to examples. It will be obvious to those skilled in the art that these examples are illustrative purpose only and are not to be construed to limit the scope of the present invention, because these examples can be modified into other various forms.

Particularly, although the cancer preventive effects and cancer inhibitory effects of the *Taxus* cambium- or procambium-derived cell line and an extract thereof were confirmed in the following examples, it will be obvious to those skilled in the art that the use of a lysate or a culture medium of the cell line can provide the same results as those obtained using the cell line or the extract thereof.

Example 1

Preparation of *Taxus* Cambium- or Procambium-Derived Cell Line 1-1: Preparation of Plant Material Each of the twig and stem of *Taxus* spp. was collected, and then immediately soaked in 100 mg/L of the antioxidant, L-ascorbic acid (DUCHEFA, The Netherlands). Then, they were transported and stored.

Then, the plant was pretreated with a mixed solution of 1% benomyl (Dongbu Hannong Chemical, Korea), 1% daconil (Dongbu Hannong Chemical, Korea), 1% sterptomycin sulphate (DUCHEFA, The Netherlands) and 0.1% cefotaxime sodium (DUCHEFA, The Netherlands) for 24 hours, and then washed with tap water for 30 minutes to remove phenolic compounds and the remaining chemicals. Then, the plant was surface-sterilized in 70% ethanol (DC Chemical, Korea) for 1 min, 30% hydrogen peroxide (LG Chemical, Korea) for 15 min, 1% CLOROX solution for 15 min and 3% CLOROX solution for 5 min, and then washed 3-4 times with water.

1-2: Isolation of Procambium and Cambium Tissues from Twig and Stem

The outer tissues of the twig and stem, which have undergone the sterilization process, were readily peeled by pulling them in the lengthwise direction. The peeled tissues were composed of xylem, procambium (twig) or cambium (stem), phloem, cortex and epidermis, and they were cultured in such a manner that the innermost tissue of the peeled tissues, that is, xylem, came into contact with a medium.

1-3: Induction of *Taxus* Procambium- and Cambium-Derived Cell Lines

At 4-7 days of initial culture, the division of cells from procambium and cambium was visually observed, and after 15 days of culture, amorphous callus formed by dedifferentiation started to be induced from the layer composed of phloem, cortex and epidermis. However, cell division in xylem did not occur throughout the culture period, and thus cambium layer was naturally separated from the xylem. After 30 days of culture, the tissue started to be separated into a cambium layer and a phloem-containing upper layer, that is, an amorphous callus layer (FIG. 1(*a*)), and after the tissue was naturally completely separated into the two layers, the layers were separately cultured in different Petri dishes (FIG. 1(*b*)). In FIG. 1(*a*), the top indicates a tissue containing phloem, cortex and epidermis, the middle indicates cambium, the bottom indicates xylem, and the arrow head indicates the separation between the cambium layer and the tissue containing phloem, cortex and epidermis. In FIG. 1(*b*), "A" indicates a phloem/cortex/epidermis-containing tissue-derived cell line, which proliferated irregularly due to the difference in division between cells, "B" indicates a cambium-derived cell line, which proliferated to form a uniform cell layer through regular cell division, and "C" indicates xylem in which cell division did not occur. FIG. 1(*c*) shows that a procambium-derived cell line is induced. In FIG. 1(*c*), "A" shows the twig observed after 30 days of culture and is a photograph showing that the procambium (bottom) is separated from callus cells derived from the tissue composed of primary phloem, cortex and epidermis, "B" is a photograph after 35 days of culture and shows that the induced procambium layer was isolated and cultured, and "C" is a photograph after 40 days of culture and shows that the callus of the tissue composed of primary phloem, cortex and epidermis proliferated after the isolation of the procambium layer.

After the tissue was isolated as described above, the white and friable portion thereof having good growth rate was subcultured in the same fresh medium as induction medium at an interval of 21 days. Meanwhile, the medium used to induce only the procambium- and cambium-derived cell lines is shown in Table 1 below.

The growth regulator auxin was added to the medium at a concentration of 1-3 mg/L. The culture was carried out in a dark room controlled at 25±1° C.

TABLE 1

Medium for inducing cell lines from *Taxus* spp. (medium 1)

| | Composition | Contents(mg/L) |
|---|---|---|
| Inorganic salts | KNO$_3$ | 1011.1 |
| | MgSO$_4$•7H$_2$O | 121.56 |
| | MnSO$_4$•4H$_2$O | 10 |
| | ZnSO$_4$•7H$_2$O | 2 |
| | CuSO$_4$•5H$_2$O | 0.025 |
| | CaCl$_2$•2H$_2$O | 113.23 |
| | KI | 0.75 |
| | CoCl$_2$•6H$_2$O | 0.025 |
| | NaH$_2$PO$_4$•H$_2$O | 130.44 |
| | H$_3$BO$_3$ | 3 |
| | Na$_2$MoO$_4$•2H$_2$O | 0.25 |
| | FeNaEDTA | 36.7 |
| Vitamin | Myo-inositol | 450 |
| | Thaimine-HCI | 20 |
| | Nicotinic acid | 2 |
| | Pyridoxine-HCI | 2 |
| | L-ascorbic acid | 100 |
| | Citric acid | 150 |
| Phytohormone | Auxin | 1~3 |
| | Gibberellic acid | 0.5 |
| Amino acid | Casein hydrolysate | 500 |
| Sucrose | | 30,000 |
| Activalted | | 100 |
| Gelrite | | 4,000 |

For comparison, *Taxus* embryo and needle explants were sterilized, and then cultured in the medium of Table 1. As a result, it could be observed that the embryo and needle explants formed callus by dedifferentiation. The callus induced from the embryo and needle explants had an irregular shape due to the difference in division rate between various cells like the case of the phloem-containing tissue, showed unstable growth rate and readily turned brown. The brown and aggregated callus induced from the embryo and needle explants showed slow growth due to phenolic compounds secreted therefrom, and ultimately died. Namely, after 6 months of culture, the callus induced from the embryo and needle explants were difficult to maintain and culture. However, the procambium- and cambium-derived cells were stably maintained without variations in their growth rate, growth pattern and aggregation, when they were cultured for a long period of more than 20 months, suggesting that the large scale cell culture was possible.

1-4: Observation of Growth and Characteristics of Isolated Cell Lines

The procambium- and cambium-derived cell lines were placed in a flask containing a liquid medium shown in Table 2 below. Then, the cell lines in the flask were cultured in a rotating shaker at 100 rpm at 25±1° C. The subculture was set to 2 weeks, such that the cultured cells could always maintain high viability in the exponential growth phase.

TABLE 2

Suspension medium for cell lines from *Taxus* spp. (medium 2)

| | Composition | Contents(mg/L) |
|---|---|---|
| Inorganic salts | KNO$_3$ | 1011.1 |
| | MgSO$_4$•7H$_2$O | 121.56 |
| | MnSO$_4$•4H$_2$O | 10 |
| | ZnSO$_4$•7H$_2$O | 2 |
| | CuSO$_4$•5H$_2$O | 0.025 |
| | CaCl$_2$•2H$_2$O | 113.23 |
| | KI | 0.75 |
| | CoCl$_2$•6H$_2$O | 0.025 |
| | NaH$_2$PO$_4$•H$_2$O | 130.44 |
| | H$_3$BO$_3$ | 3 |
| | Na$_2$MoO$_4$•2H$_2$O | 0.25 |
| | FeNaEDTA | 36.7 |
| Vitamin | Myo-inositol | 200 |
| | Thaimine-HCI | 20 |
| | Nicotinic acid | 2 |
| | Pyridoxine-HCI | 2 |
| | L-ascorbic acid | 100 |
| | Citric acid | 150 |
| Phytohormone | Auxin | 1~3 |
| | Gibberellic acid | 0.1 |
| Amino acid | Apartic acid | 133 |
| | Arginine | 175 |
| | Proline | 115 |
| | Glycine | 75 |
| Sucose | | 20,000 |

Meanwhile, the embryo- and needle-derived callus were also cultured in medium 2 of Table 2 and compared with the procambium- and cambium-derived cell lines of the present invention.

The degree of aggregation of the cells was observed with biological microscope CX31 (Olympus, Japan). As a result, as shown in Table 3 below, it could be seen that more than 90% of cells of the cell lines according to the present invention were present as single cells upon suspension culture. As shown in FIG. 1(d), it could be observed that the cell lines according to the present invention were morphologically characterized by a large number of vacuoles and were in an undifferentiated state. The arrow in FIG. 1(d) indicates vacuoles in the *Taxus* procambium-derived cells.

TABLE 3

The type of cell aggregates of *Taxus* long-term cultures

| Large cell aggregates | Moderate cell aggregates | Small cell aggregates | Single cell population | Explant source |
|---|---|---|---|---|
| 60 ± 3.2% | 30 ± 3.3% | 7 ± 0.6% | 3 ± 0.9% | embryo |
| | | | | needle |
| 0 | 0 | 9% | 91% | cambium |
| 0 | 0 | 7.4 ± 0.8% | 92.6 ± 0.8% | procambium |

Large cell aggregates, size higher than 1.5 × 10$^3$ μm;
Moderate cell aggregates 1 × 10$^3$ μm;
Small cell aggregates 4 × 10$^2$ μm < size < 1 × 10$^3$ μm Meanwhile, in order to examine the possibility of large scale cell culture, the embryo/needle-derived callus and the procambium- and cambium-derived cells were cultured in an airlift bioreactor (Sung-Won Cytec, Korea) having an internal volume of 3 L. The culture was carried out in the liquid medium of Table 2 under dark conditions at 25±1° C.

As a result, as can be seen in Table 4 below, it was observed that the doubling time of the *Taxus* procambium- and cambium-derived cell cultures according to the present invention was 4-5 days in the bioreactor, which did not differ from that in the flask or was shortened compared to that in the flask, whereas the doubling time of the heterogeneous cell lines, that are embryo/needle-derived cell cultures was 12 days in the flask, but was 21 days in the bioreactor. In other words, it was seen that, when cultured in the flask, the cell lines according to the present invention showed about 2-3-folds higher growth rate compared to cell lines derived from tissues other than the procambium or cambium of *Taxus*, and when cultured in the bioreactor, the cell lines according to the present invention showed 5-6-folds higher growth rate compared to cell lines derived from tissues other than the procambium or the cambium. This is believed to be because cell viability rapidly decreased due to growth ring formation in the bioreactor, plant cell aggregation during culture, and the sensitivity of rigid cell walls to shear stress.

The procambium- and cambium-derived cell lines according to the present invention formed a very small growth ring area in the bioreactor, and the ring formed on the internal wall thereof was simply eliminated, when a simple stimulus was applied to the incubator to shake the medium. Also, it was shown that the inventive cell lines had low aggregation and contained a large number of vacuoles, and thus had low sensitivity to shear stress, such that cell viability did not decrease. In other words, it was seen that the cell lines according to the present invention had low sensitivity to shear stress resulting from shaking in the bioreactor for mass production, and thus could be produced rapidly in large amounts in the bioreactor. In consideration of the difference in growth rate of the cell lines between the flask culture and the bioreactor culture, it could be seen that the *Taxus* procambium- or cambium-derived cell line according to the present invention had 2-3-folds lower sensitivity to shear stress compared to cell lines derived from tissues other than the procambium or cambium of *Taxus*.

TABLE 4

| Explant source | Doubling time (day) | |
|---|---|---|
| | flask | bioreactor |
| embryo | 11.5 ± 1.3 | 21 ± 2.6 |
| needle | 12 ± 2 | 21 ± 2 |
| procambium, cambium | 5 ± 0.2 | 4 ± 0.1 |

1-5: Treatment with Sugar and Methyl Jasmonate

The cell lines, which have been suspension-cultured for 14 days as described in Example 1-4, were cultured in media (containing sterile water, 3-5 wt % (g/L) of raw sugar and 100 µM of methyl jasmonate) for 10 days in dark conditions, and then the cells were collected and used in the subsequent experiments.

Example 2

Preparation of extract of *Taxus* Procambium- or Cambium-Derived Cell Line

From the cell line prepared in Example 1, active ingredients were extracted stepwise as follows.
(i) 500 g of the cell line from which the medium has been removed was dissolved in 500 ml of distilled water at 50° C. for 6 hours while being stirred.
(ii) After completion of the dissolution, the cell solution was centrifuged at 3,000 g for 10 minutes, and the supernatant was collected, thus obtaining a distilled water-soluble substance.
(iii) After obtaining the distilled water-soluble substance, the remaining distilled water-insoluble substance was dissolved in 500 ml of methanol at room temperature for 6 hours while being stirred.
(iv) After completion of the dissolution, the solution was centrifuged at 3,000 g for 10 minutes, and the supernatant was collected, thus obtaining a methanol-soluble substance.
(v) After obtaining the methanol-soluble substance, the remaining methanol-insoluble substance was dissolved in 500 ml of acetone at room temperature for 6 hours while being stirred.
(vi) After completion of the dissolution, the solution was centrifuged at 3,000 g for 10 minutes, and the supernatant was collected, thus obtaining an acetone-soluble substance.
(vii) The distilled water-, methanol- and acetone-soluble substances obtained as described above were concentrated using a rotary vacuum evaporator.
(viii) The concentrated samples were dried using a freeze dryer and dissolved in distilled water, methanol and acetone, thus obtaining a distilled water extract, methanol extract and acetone extract of the cell culture.

Example 3

Measurement of Antioxidant Activity of *Taxus* Cambium- or Procambium-Derived Cell Line Extract Because the correlation between an antioxidant effect and the prevention of cancer is known, the following test was carried out in order to examine whether the cell line according to the present invention has the effect of preventing cancer.
3-1: Culture of Human Diploid Fibroblasts (HDF)

HDF cells were isolated from the fetal penis prepuce and cultured. The culture medium was prepared by adding 10% fetal bovine serum (FBS, Hyclone, Logan, Utah, USA) inactivated by heating at 56° C. for 30 minutes, 100 unit/ml of penicillin, 100 µg/mk of streptomycin and 300 µg/ml of glutamine to DMEM medium (Invitroge Gibco life tech. Vienna, Austria). The cells were cultured in the medium, described above, in a 5% $CO_2$ incubator at a temperature of 37° C. and a humidity of 95% and subcultured at 3-4-day intervals, immediately before the cells were fused with each other. The subcultured cells were divided, according to the number of subcultures (passages), into young cells cultured less than 20 passages, middle cells cultured for 21-49 passages, and aged cells cultured more than 50 passages.

3-2: Measurement of Reactive Oxygen Species Induced by $H_2O_2$

In order to examine whether reactive oxygen species induced by $H_2O_2$ are inhibited when skin diploid fibroblasts (HDF cells) are treated with the distilled water extract among the extracts obtained in Example 2, the measurement of reactive oxygen species (ROS) was carried out.

The measurement of intracellular reactive oxygen species was carried out by Facscan analysis using a DCFDA (2',7'-dichlorofluorescin diacetate, Fluka Cat 35847 Molecular Probes, USA) fluorescent dye sensitive to reactive oxygen species. HDF cells according to each PD were grown on a 100-mm plate, and then incubated with 5 uM of DCFDA in dark conditions at 37° C. for 30 minutes. Then, the cells were washed twice with PBS and collected by treatment with trypsin-EDTA. Then, the cells were collected by centrifugation at 900 rpm for 4 minutes, and then reactive oxygen species per 10,000 cells were measured (FIGS. 2(*a*) and 2(*b*)).

$5 \times 10^5$ cells were dispensed into a 6-well plate, and then treated with $H_2O_2$ alone or in combination with the extract obtained in Example 2. As the extract, the distilled water extract among the extracts obtained in Example 2 was used at a concentration of 10-100 µg/ml, and preferably 50 µg/ml. Then, the cells were washed 2-3 times with HBSS (Hank's balanced salt solution) and stabilized in HBSS for about 30 minutes. Then, the cells were stained with 10 µM of DCFDA (Molecular Probes USA) in dark conditions at 37° C. for 1 hour, washed three times with HBSS, and then observed with a fluorescent microscope (FIG. 2(*c*)).

As described above, the HDF cells were treated with 200 µM of $H_2O_2$ and 10-100 µg/ml (preferably 50 µg/ml) of the distilled water extract obtained in Example 2, and the variation in the morphology of the cells was observed.

At 24 hours after the treatment of the cells with $H_2O_2$, the HDF cells generate reactive oxygen species (ROS) by oxidative stress. Because non-fluorescent DCFDA is oxidized by reactive oxygen species to form DCF showing strong fluorescence, reactive oxygen species can be measured. In this Example, FACS Calibur (Becton Dickinson Analytic Flow Cytometer, USA) was used for measurement.

Figure 2:
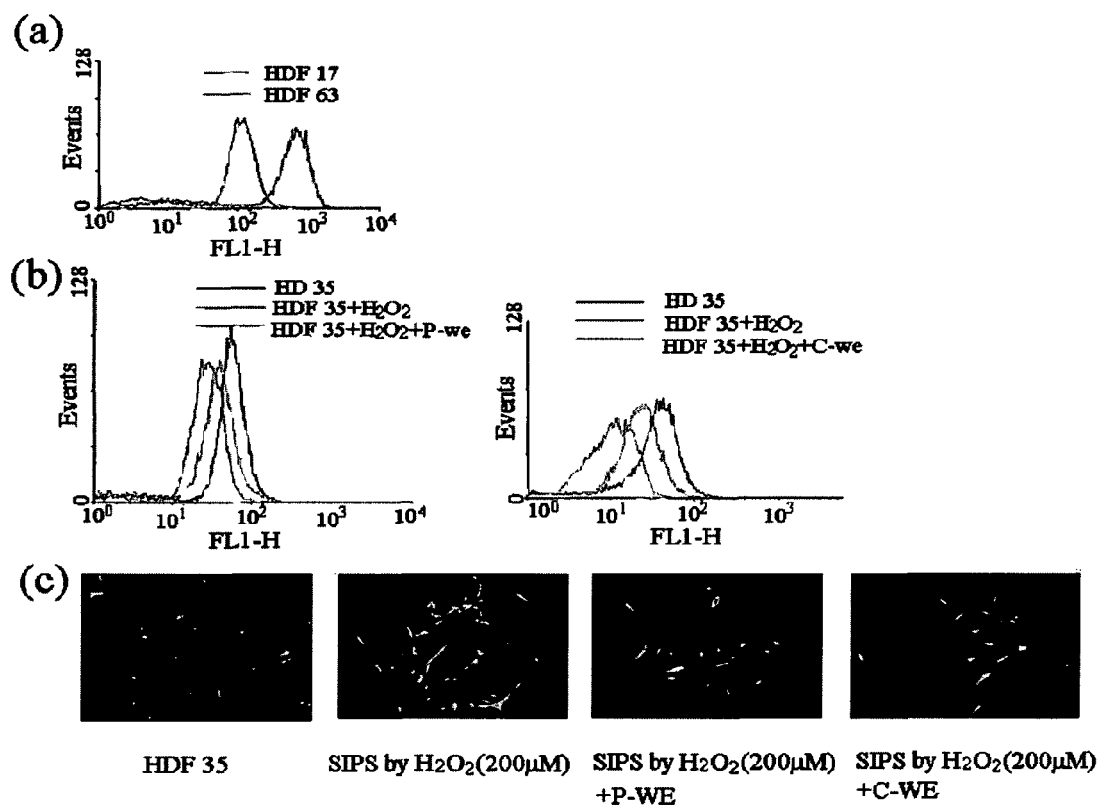
FIG. 2(a) illustrates the reactive oxygen species per 10,000 cells for HDF 17 and HDF 63 cells.
FIG. 2(b) illustrates the reactive oxygen species per 10,000 cells for HDF 35 cells induced to age using $H_2O_2$.
FIG. 2(c) illustrates the DCFH fluorescence photographs which show the antioxidant activity of cell line extracts according to the present invention, when the aging of HDF 35 cells are induced by treatment with $H_2O_2$.
FIG. 2(d) shows the PDA spectrum of the cell line extract.

As a result, as shown in FIG. 2, the *Taxus* cambium-derived cell line extract and the *Taxus* procambium-derived cell line extract all inhibited the production of reactive oxygen species (ROS). In FIG. 2, P-WE: procambium-distilled water extract, and C-WE: cambium-distilled water extract. Namely, it could be observed that the two cell line extracts all inhibited the production of reactive oxygen species.

Substances having excellent antioxidant activity are active substances that inhibit cellular damage caused by cellular oxidation, and reactive oxygen species (ROS) produced in vivo bind to cellular molecules, such as intracellular DNA, proteins and lipids, to cause cellular mutations, and are involved in the formation of cancer tissue by inhibiting the normal function of cells.

Accordingly, because it was found in the above experiment that the *Taxus* cambium-derived cell line and procambium-derived cell line of the present invention had antioxidant effects, the *Taxus* cambium-derived cell line and procambium-derived cell line of the present invention have the effect of preventing cancer.

Example 4

Anticancer Activity by Administration of Cell Lines Derived from *Taxus* Cambium and Procambium (1) In this experiment, Balb/C mice purchased from Damool Science (Daejeon, Korea) were bred according to general animal breeding regulations. Specifically, 6-week-old mice were purchased and adapted for about 5 days. Then, $1 \times 10^6$ CT-26 colon cancer cells (Korean Cell Line Bank KCLB80009) were injected subcutaneously into the right portion of the mouse back.

At about 3 days after the injection of the cancer cells, the growth of the cancer cells to a size approximately equal to the size of hulled millet was observed. Thus, from 3 days after the injection of the cancer cells, the each of the cambium-derived cell line and procambium-derived cell line obtained in Example 1 were freely fed to the mice. A control group was fed with a conventional nutrient-containing mouse feed, and the administration of the cell lines was performed by finely crushing the same feed, adding the cell line thereto at a ratio of 1:1, preparing a feed having the same shape as that of the conventional feed, and allowing the mice free access to the prepared feed. Herein, the average daily dosage of the cell line was 2-3 g of cell fresh weight/mouse. All other conditions were the same between the control group and the test group, and the size of the cancer cells was observed for 3 weeks. In the experiment, each of the control group and the cell line-fed group consisted of 15 animals (7 animals for the cambium-derived cell line, and 8 animals for the procambium-derived cell line), and the experiment was repeated 3 times.

(2) Results of Observation of Cancer Cell Size after Administration of Cell Line for Three Weeks.

Figure 3:
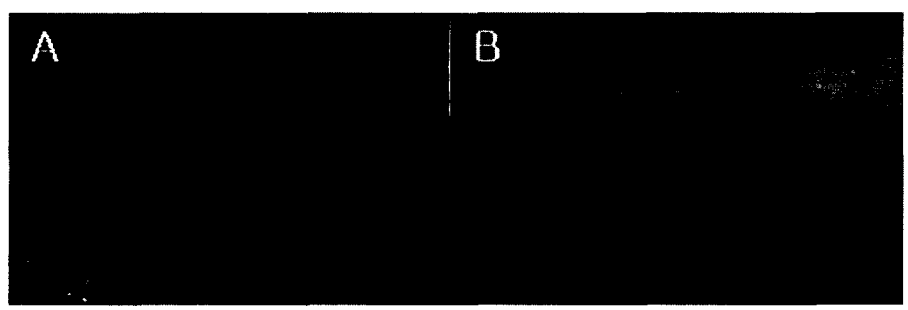
FIG. 3 depicts photographs showing the comparison of the size of cancer tissue between a control group (A) and cell line-administered group at 2 weeks after administration of the cell line (B) according to the present invention.

At 2 weeks after administration of the cell lines according to the present invention, the size of cancer tissue in the model mice was observed. As a result, as shown in FIG. 3, it could be observed that the growth of cancer tissue in the group administered with the cambium-derived cell line and the procambium-derived cell line was inhibited compared to the control group.

Figure 4:
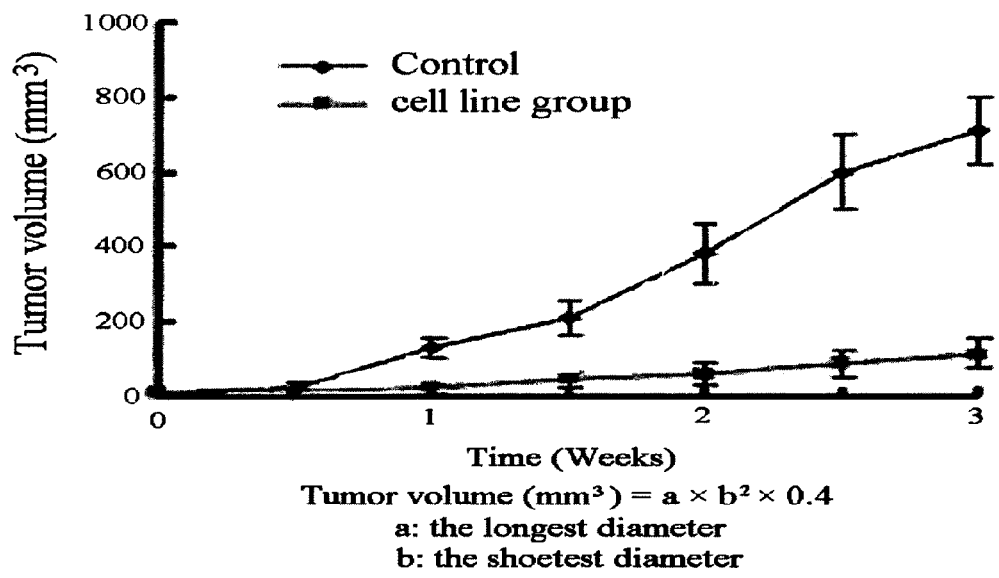
FIG. 4 is a graphic diagram showing the volumes of a control group and a cell line-administered group for 3 weeks after administration of a cell line according to the present invention.
Figure 5:
FIG. 5 is a photograph of cancer tissues resected from mice of a control group (A) and a cell-administered group at 3 weeks after administration of the cell line (B) according to the present invention.

Also, as shown in FIG. 4, at 3 weeks after administration of the cell lines, the volume of cancer tissue in the group administered with the cell lines was about 100 $mm^3$, but the control group showed a cancer tissue volume which was more than 6-folds larger than that of the cell line-administered groups. In addition, the cancer tissues were resected and photographed and, as a result, as shown in FIG. 5, there was a significant difference in volume between the control group and the cell line-administered group. The weight of the resected cancer tissues was measured and, as a result, it was observed that the average weight of the cancer tissues in the control group was 2.16 g, whereas the average weight of the cancer tissues in the cell line-administered group was 0.21 g which was about 1/10 of that of the control group. Accordingly, it could be found that the cell lines according to present invention inhibited the general growth of cancer cells, suggesting that these cell lines had the effect of preventing and treating cancer.

(3) Meanwhile, cancer tissues were resected from the control group and the cell line-administered group, and then the internal tissues thereof were observed at various magnifications. The observation results are shown in FIG. 6.

Figure 6:
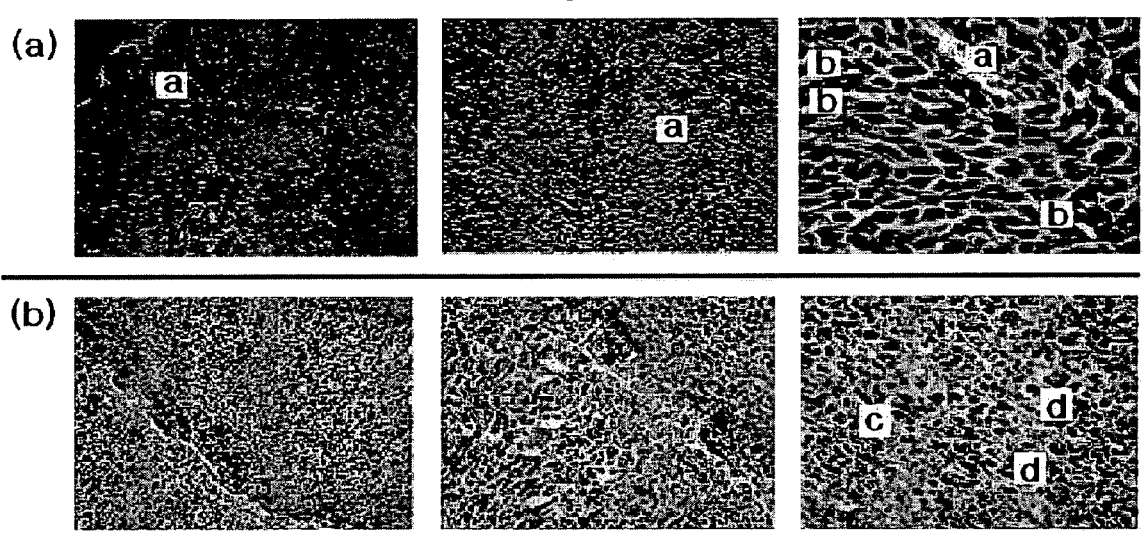
FIG. 6 is a photograph of the internal tissue of the resected cancer tissue of a control group (A) and at 3 weeks after administration of the cell line (B) according to the present invention.

In the observation results, the control group showed characteristics in that there was no region showing cell death called apoptosis, the tissue in the whole region was dense, and dividing cells (portions indicated by "b" in FIG. 6(*a*)) were large. The fact that the dividing cells were large means that the cancer tissue in the control group continued to grow and expand.

However, in the cell line-administered group, the tissue was not dense, and most cells showed the condensation of nuclei called apoptotic bodies (portions by indicated "c" in FIG. 6(*b*)) or division into various tissues. Such apoptotic bodies did not substantially appear in the control group.

In addition, a very characteristic phenomenon is the staining of erythrocyte (portions indicated by "a" in FIG. 6(*a*)), which show blood vessels in tissue. The control group showed many blood vessels, but the cell line-administered group did not show blood vessels. In the cell line-administered group, cells showing round nuclei predicted to be immune cells were significantly observed (portions indicated by "d" in FIG. 6(*b*)), but were not substantially observed in the control group.

Accordingly, it can be seen that the *Taxus* cambium- or procambium-derived cell line of the present invention is involved directly in the growth of cancer to induce cell death, suggesting that it has the effect of preventing and treating cancer by inhibiting the general growth of cancer tissue. In addition, it can be seen that it inhibits angiogenesis occurring in carcinogenesis and enhances the infiltration of immune cells into cancer tissue to induce strong immune activity, thus showing strong anticancer activity.

Example 5

Preparation and Cancer Cell-Killing Activity of *Taxus* Cambium- or Procambium-Derived Cell Line Extract (1) Cancer Cell Culture Human cancer cell lines: oral cavity carcinoma cell line (KB cell, Korean Cell Line Bank KCLB10017), lung cancer cell line (HCC95, Korean Cell Line Bank KCLB70095), prostate cancer cell line (PC-3, Korean Cell Line Bank KCLB21435), osteosarcoma cell line (U2-OS, Korean Cell Line Bank KCLB30096), leukemia cell line (K-562, Korean Cell Line Bank KCLB 10243), uterine cancer cell line (HeLa, Korean Cell Line Bank KCLB 10002), skin cancer cell line (HT1080, Korean Cell Line Bank KCLB10121), pancreas cancer cell line (MIA CaPa-2, Korean Cell Line Bank KCLB21420), breast cancer cell line (MCF-7, Korean Cell Line Bank KCLB30022), gastric cancer cell line (AGS, Korean Cell Line Bank KCLB21739), renal cancer cell line (Caki-1, Korean Cell Line Bank KCLB30046), and liver cancer cell line (HepG2, Korean Cell Line Bank KCLB88065).

Mouse cancer cell lines: skin cancer cell line (B16F10, Korean Cell Line Bank KCLB8008), and colon cancer cell line (CT-26, Korean Cell Line Bank KCLB 80009).

Cell culture: Each of the cell lines was cultured in RPMI or DMEM medium depending on the kind of cells. To the medium, 10% fetal bovine serum (FBS), inactivated by heating at 56° C. for 30 minutes, penicillin (100 unit/ml), streptomycin (100 µg/ml) and 300 µg/ml, of glutamine were added. Each of the cell lines was cultured in the medium in a 5% $CO_2$ incubator at 37° C. and a humidity of 95%, and subcultured at 3-4-day intervals, immediately before the cells were fused with each other. In the experiment, only cells subcultured a total of less than 30 passages were used.

Treatment with extract and measurement of cell-killing activity: $1 \times 10^5$ cells were cultured in a 6-well plate, and after 6 hours when the cells are completely adhered to the 6-well plate, the cells were treated with each of the distilled water, methanol and acetone extracts (150, 400, 800 µg/ml culture). Then, the degree of cell death was measured for 3 days after treatment with the extracts. The proliferation of the cells was measured according to the MTT assay (3-[4,5-dimethylthiazol-2-yl]-2,5-diphenyltetrazolium bromide) method.

The degree of a decrease in cell growth in the group treated with the extract was compared with a control group treated with nothing, a vehicle group having methanol and acetone added thereto, and a positive control group treated with *Taxus*-derived paclitaxel (Sigma) as an anticancer agent. The cells were washed twice with a cell culture medium warmed to 37° C. for a given time, and then 1 ml of MTT solution (5 mg/ml, without phenol red) was added thereto. Then, the cells were cultured again for 4 hours. The supernatant was removed, and the produced formazen precipitate was dissolved in 1 ml of DMSO and measured for absorbance at 570 nm. The number of survived cells was observed by fixing the cells with 50% methanol at 3 days after treatment with the extract and staining the adhered survived cell with crystal violet.

(2) Test Results Obtained by Treatment with Extract

Survived cells at 3 days after cells are treated with each of distilled water, methanol and acetone extracts (800 µg/ml)

Figure 7:
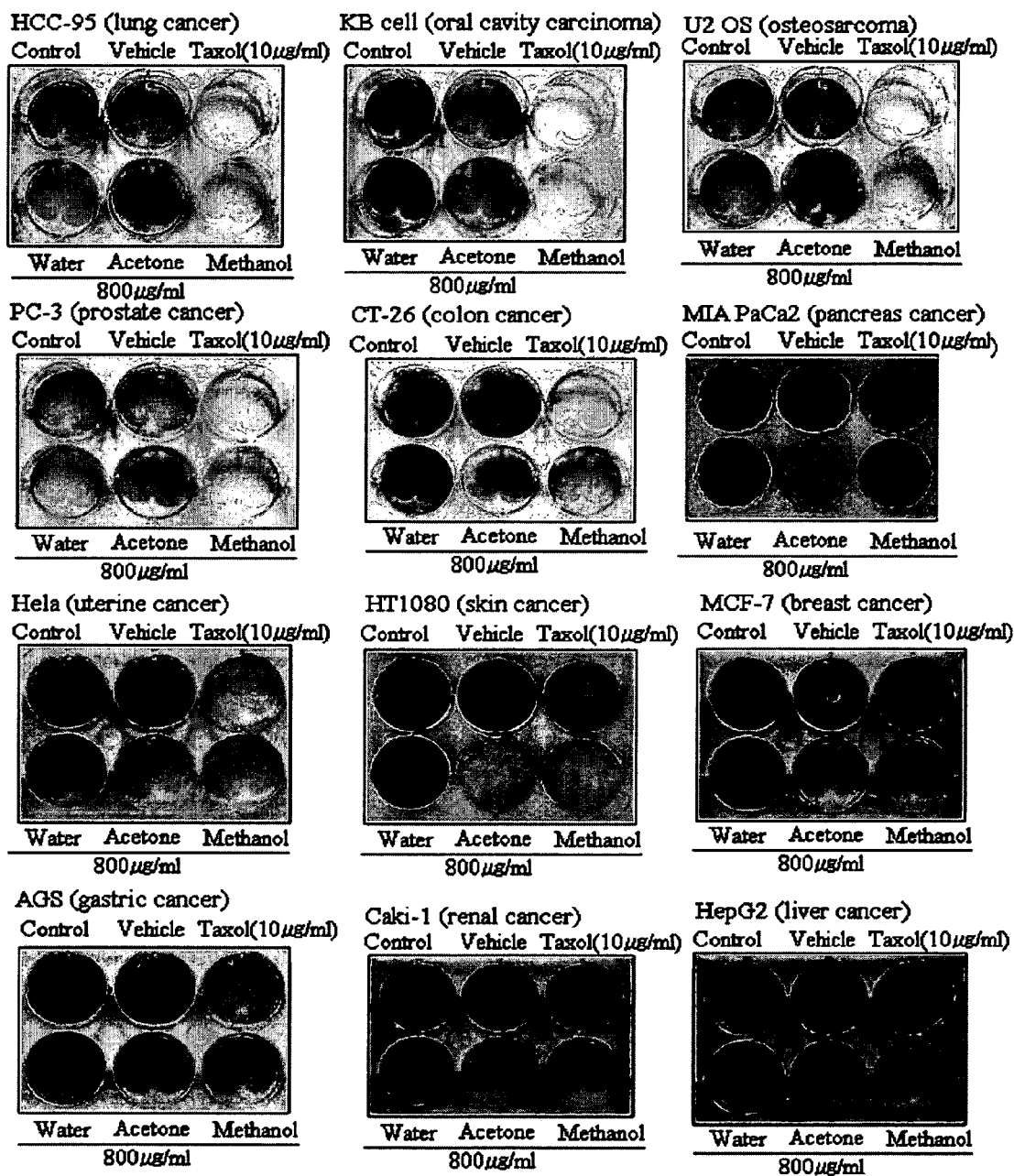
FIG. 7 depicts photographs showing the degree of cell death after the treatment of cancer cell lines with the cell line extract according to the present invention.
Figure 8:
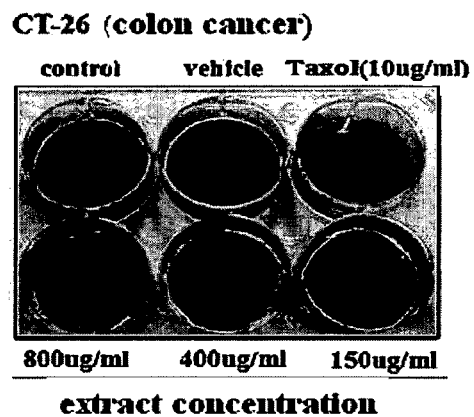
FIG. 8 is a photograph showing the degree of cell death after the treatment of a colon cancer cell line with various concentrations of a methanol extract of the cell line according to the present invention.
Figure 8:
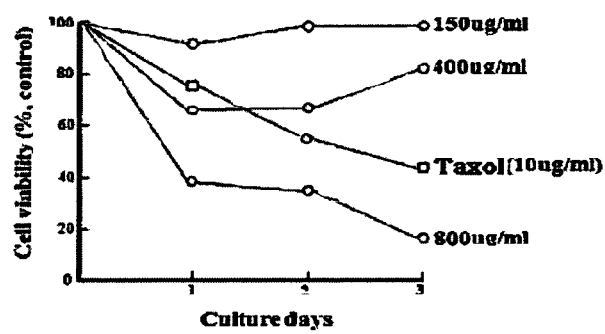
Figure 9:
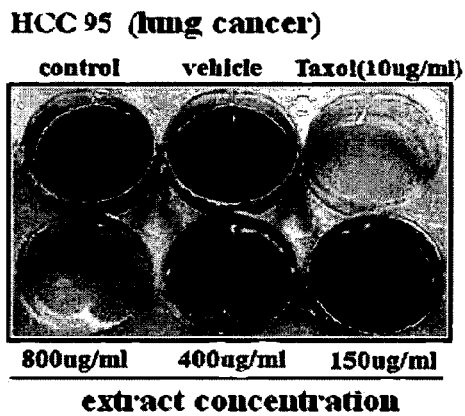
FIG. 9 is a photograph showing the degree of cell death after the treatment of a lung cancer cell line with various concentrations of a methanol extract of the cell line according to the present invention.
Figure 9:
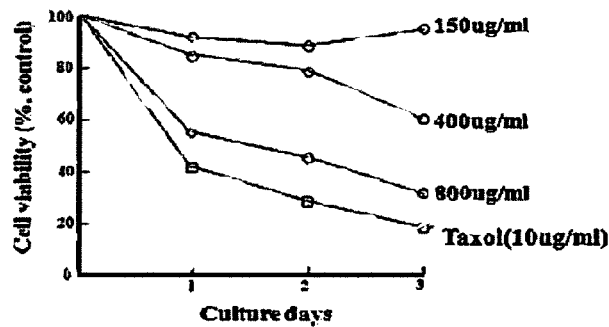
Figure 10:
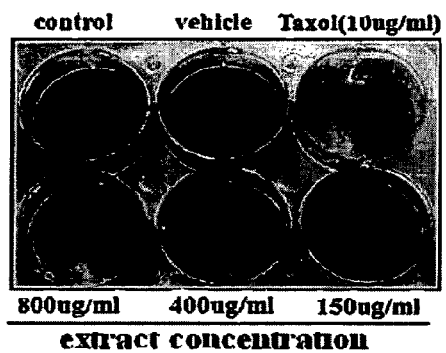
FIG. 10 is a photograph showing the degree of cell death after the treatment of a prostate cancer cell line with various concentrations of a methanol extract of the cell line according to the present invention.
Figure 10:
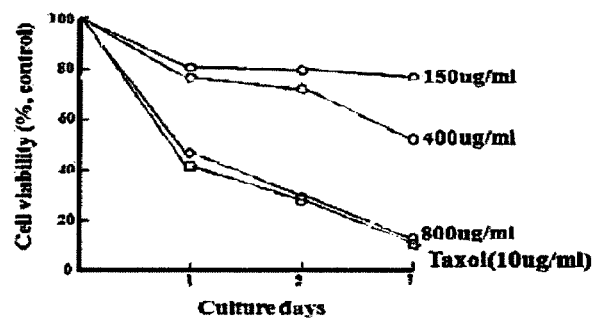
Figure 11:
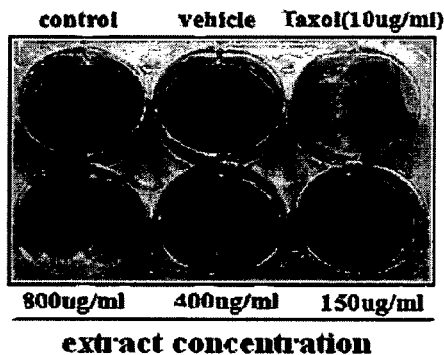
FIG. 11 is a photograph showing the degree of cell death after the treatment of an osteosarcoma cell line with various concentrations of a methanol extract of the cell line according to the present invention.
Figure 11:
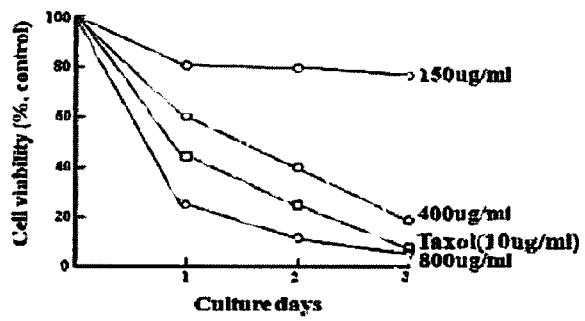
Figure 12:
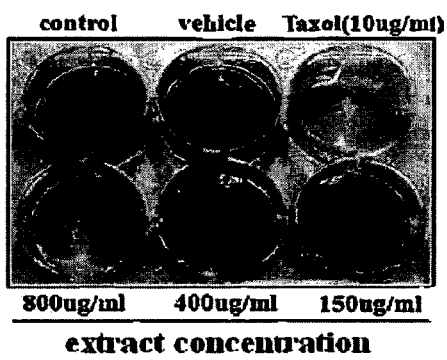
FIG. 12 is a photograph showing the degree of cell death after the treatment of an oral cavity carcinoma cell line with various concentrations of a methanol extract of the cell line according to the present invention.
Figure 12:
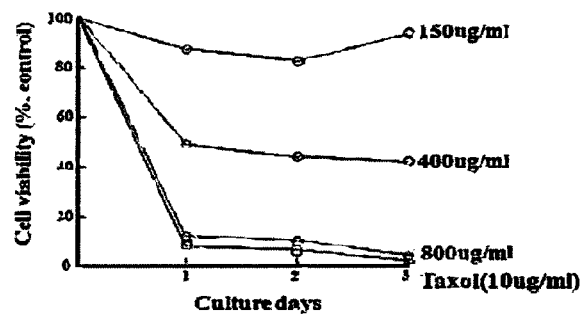
Figure 13:
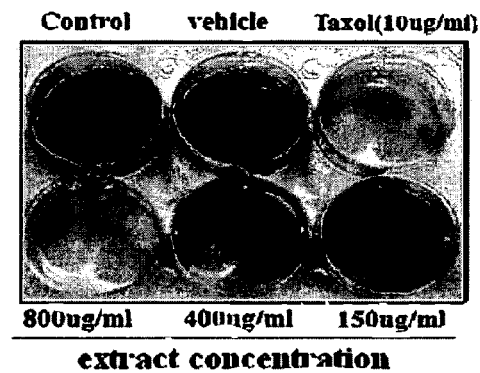
FIG. 13 is a photograph showing the degree of cell death after the treatment of a skin cancer cell line with various concentrations of a methanol extract of the cell line according to the present invention.
Figure 13:
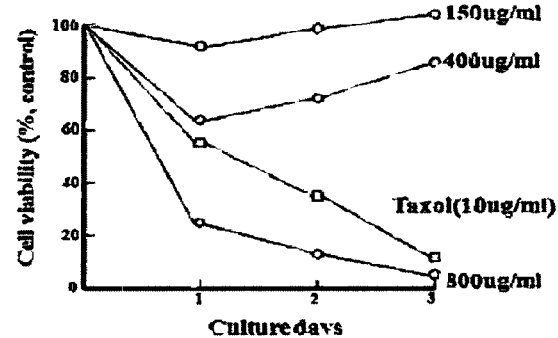
Figure 14:
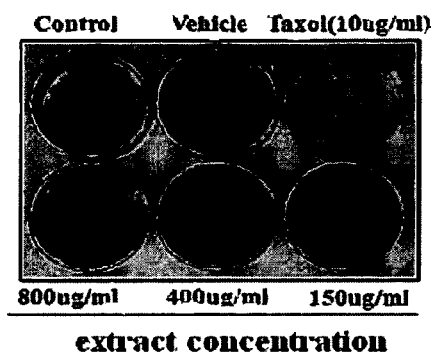
FIG. 14 is a photograph showing the degree of cell death after the treatment of a leukemia cell line with various concentrations of a methanol extract of the cell line according to the present invention.
Figure 14:
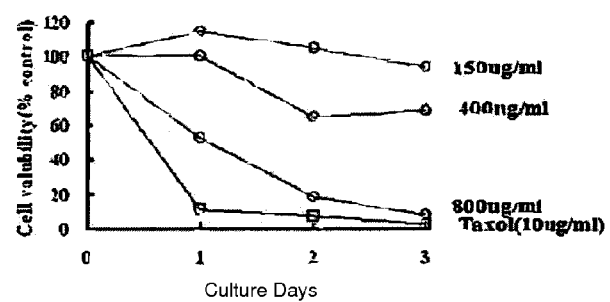
Figure 15:
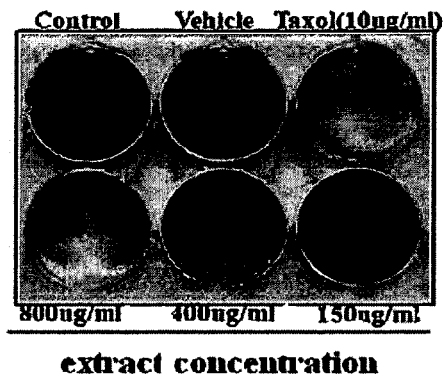
FIG. 15 is a photograph showing the degree of cell death after the treatment of a uterine cancer cell line with various concentrations of a methanol extract of the cell line according to the present invention.
Figure 15:
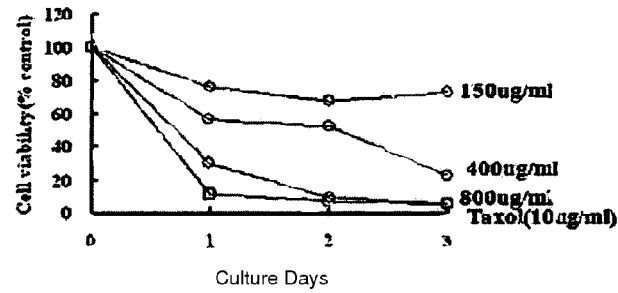
Figure 16:
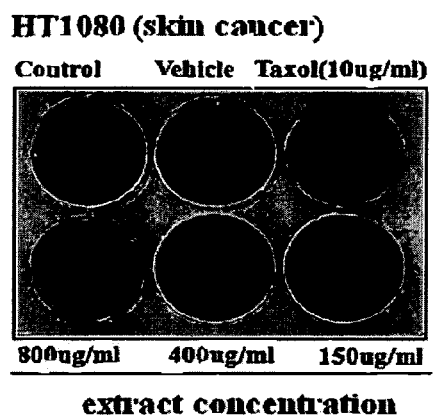
FIG. 16 is a photograph showing the degree of cell death after the treatment of a skin cancer (human) cell line various concentrations of a methanol extract of the cell line according to the present invention.
Figure 16:
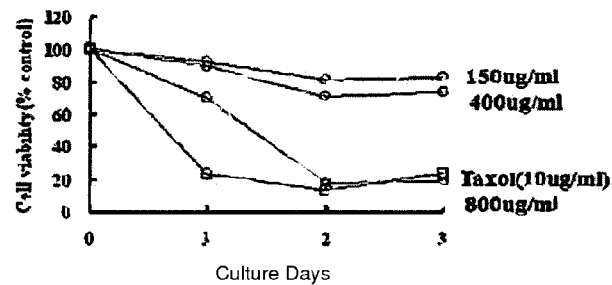
Figure 17:
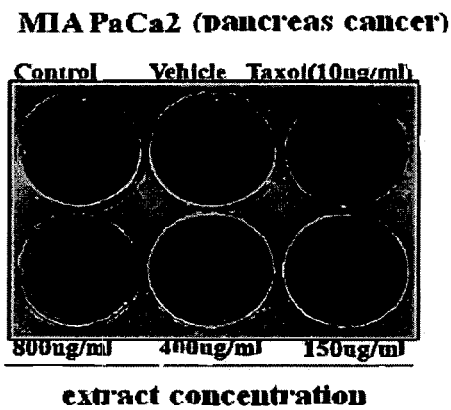
FIG. 17 is a photograph showing the degree of cell death after the treatment of a pancreas cancer cell line with various concentrations of a methanol extract of the cell line according to the present invention.
Figure 17:
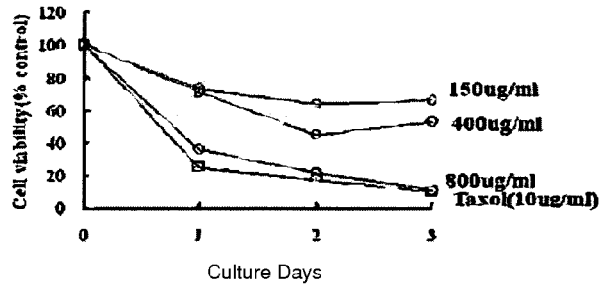
Figure 18:
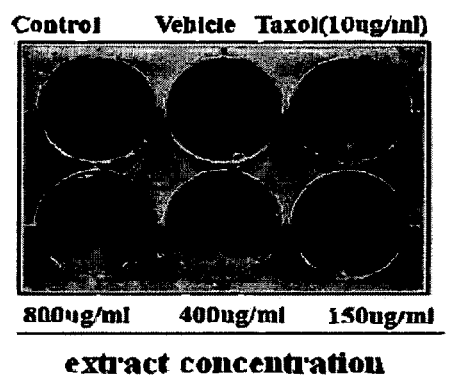
FIG. 18 is a photograph showing the degree of cell death after the treatment of a breast cancer cell line with various concentrations of a methanol extract of the cell line according to the present invention.
Figure 18:
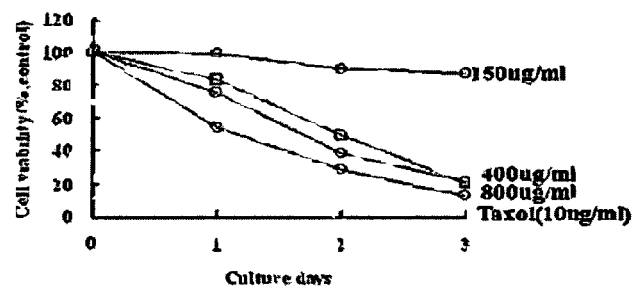
Figure 19:
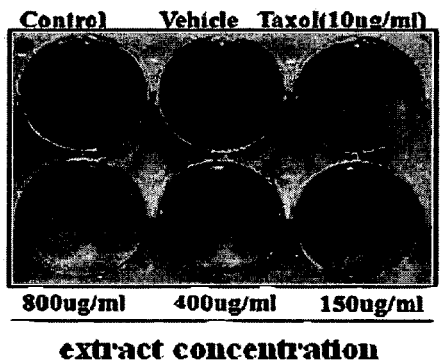
FIG. 19 is a photograph showing the degree of cell death after the treatment of a gastric cancer cell line with various concentrations of a methanol extract of the cell line according to the present invention.
Figure 19:
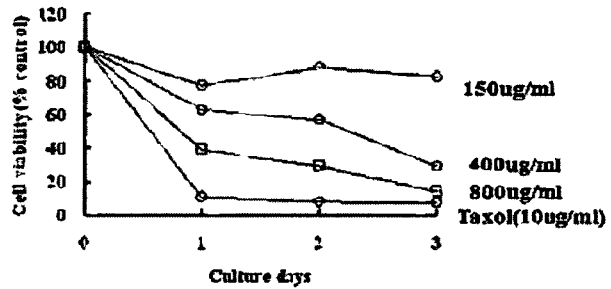
Figure 20:
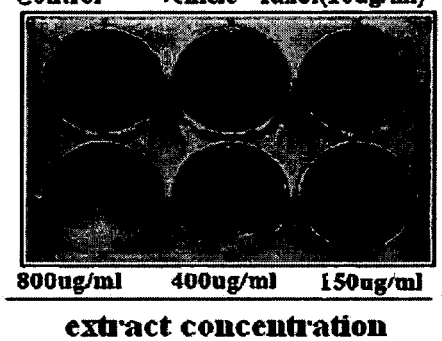
FIG. 20 is a photograph showing the degree of cell death after the treatment of a renal cancer cell line with various concentrations of a methanol extract of the cell line according to the present invention.
Figure 20:
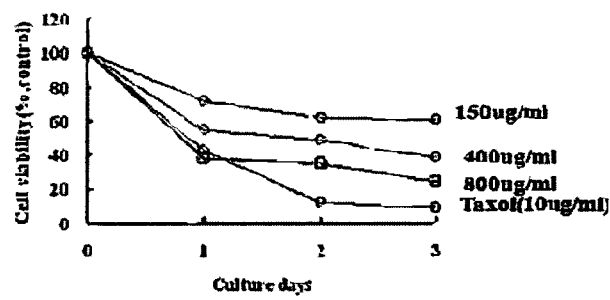
Figure 21:
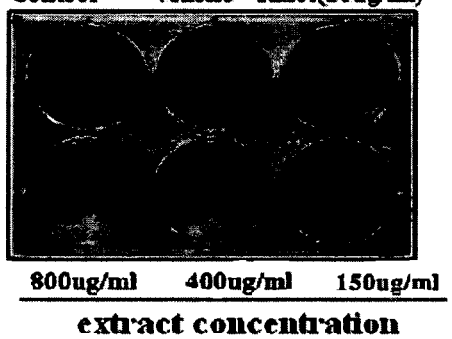
FIG. 21 is a photograph showing the degree of cell death after the treatment of a liver cancer cell line with various concentrations of a methanol extract of the cell line according to the present invention.
Figure 21:
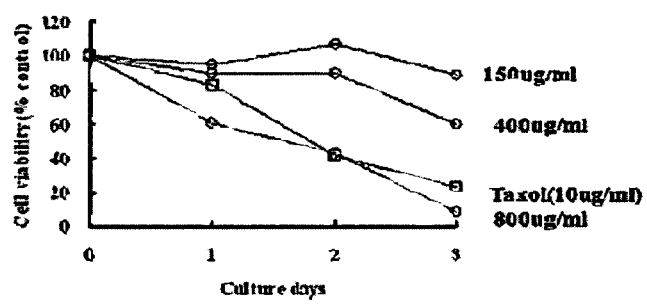

Each of the *Taxus*-derived cell lines from which the culture medium has been removed was dissolved in distilled water, methanol and acetone in sequence to obtain cell line extracts, and then cells were treated with each of the extracts. As a result, the methanol extract showed the highest apoptotic activity in most of the tested cells, and this apoptotic activity was similar to the apoptotic effect in a positive control group (Taxol (paclitaxel) of FIG. 7) treated with about 10 µg/ml of paclitaxel.

The distilled water and acetone extracts also showed apoptotic effects, but showed apoptotic activity, which was generally lower than that of the methanol extract. However, the vehicle control (vehicle FIG. 7) treated with only methanol and acetone had no effect on apoptosis. This suggests that the extracts of the cell lines contain substances showing cancer cell-killing activity. In the next step, the cells were treated with various concentrations of the methanol extract, and the degree of apoptosis of the cells was measured.

Apoptotic Activity According to Treatment with Various Concentrations of Methanol Extract The methanol extract was dissolved in methanol at a concentration of 200 mg/ml and added to each of 1 ml of the test cell line culture medium at concentrations of 150, 400 and 800 µg/ml. The growth of the cells was measured by the MTT method at a one-day interval from day 1 to day 3 after addition of the methanol extract, and at 3 days after addition of the methanol extract, the survived cells were fixed with methanol, and then stained with crystal violet. The results of measurement for the 14 cancer cell lines are shown in FIG. 8 to FIG. 21.

In the above results, the methanol extract of the *Taxus* cambium- or procambium-derived cell line according to the present invention showed apoptotic activity in the 14 cancer cell lines in a concentration-dependent manner. 800 µg/ml of the methanol extract showed strong apoptotic activity in all the cell lines, and this apoptotic activity was similar to the apoptotic activity of paclitaxel (10 µg/ml) used in the positive control group. However, in CT-26 (FIG. 8) and B16F10 (FIG. 13), 800 µg/ml of the methanol extract showed apoptotic activity higher than that of the positive control group. The quantitative difference between paclitaxel used in the positive control group and the methanol extract of the cell line according to the present invention is attributable to the fact that paclitaxel is a highly purified substance, whereas the extract of the cell line is a mixture of a large number of compounds. Accordingly, it is considered that the apoptotic activity of the cell line according to the present invention will be further improved through a purification process.

Example 6

Examination of whether *Taxus* Cambium- or Procambium-Derived Cell Line Contains Paclitaxel Meanwhile, in order to prove the fact that the anticancer activity of the cell line according to the present invention is not the activity of paclitaxel, existence of paclitaxel in the cell line of the present invention was examined in the following manner.

A paclitaxel (Taxol) standard used in this Example was purchased from Sigma, and HPLC water (J. T. Baker), acetonitrile and methanol were filtered through a 0.2 µm filter and then used as a mobile phase.

0.2 g of the cell line prepared in Example 1 was vortexed in 0.4 ml of MeOH for 5 minutes, and then extracted at room temperature for 1 hour. The extract was centrifuged at 13000 rpm for 5 minutes and filtered through a 0.2 µm filter, and the filtrate was quantitatively analyzed by UPLC.

In the UPLC (Waters, Mass., USA) analysis, the extract was quantitatively analyzed in comparison with the standard using an UPLC BEH C18 column (100 mm×2.1 mm i.d.×1.7 µm). As the mobile phase, water and acetonitrile were used at a flow rate of 0.4 mL/min in gradient elution, and UV detection was carried out at an absorbance of UV 227 nm.

Figure 22:
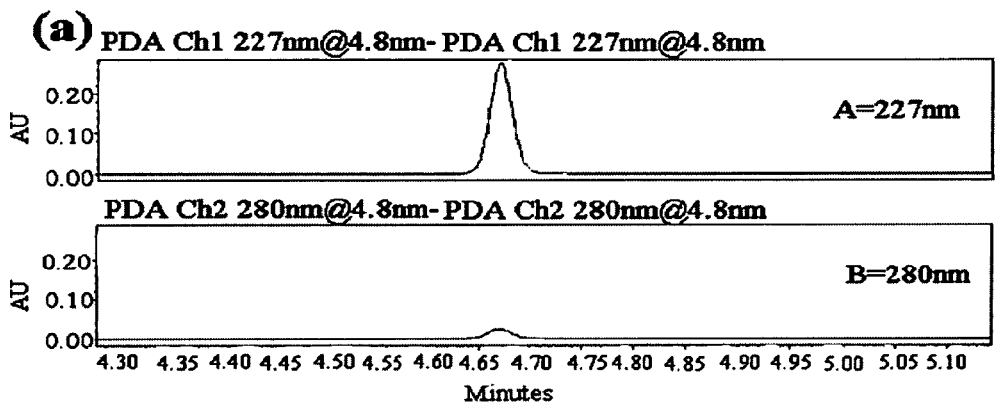
FIG. 22(a) shows the paclitaxel standard analyzed by UPLC.
FIG. 22(b) shows the cell line according to the present invention analyzed by UPLC.
Figure 22:
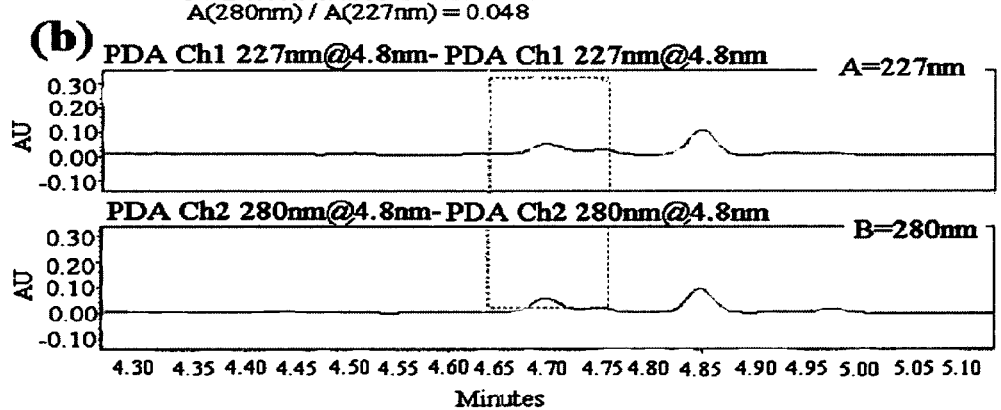
Figure 22:
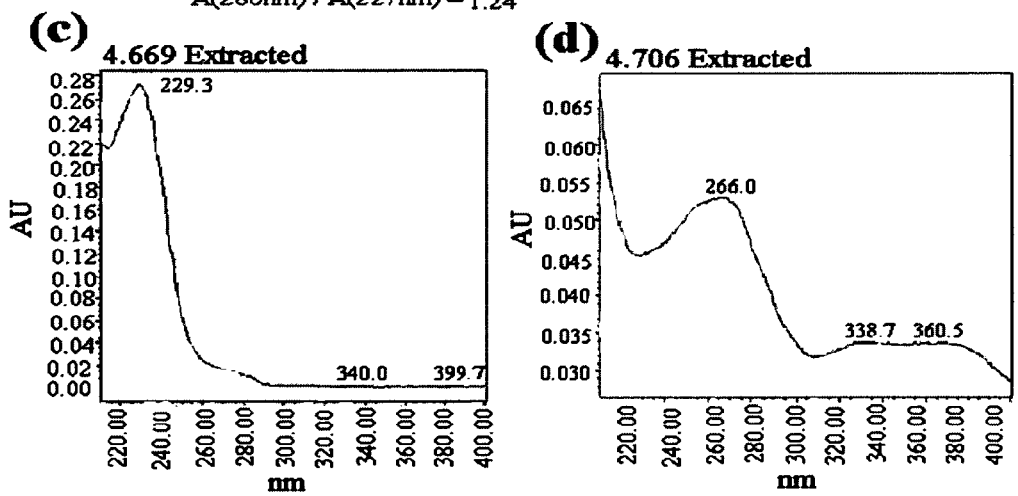

The taxol standard was analyzed by UPLC at absorbances of 227 nm and 280 nm. As a result, as shown in FIG. 22(*a*), the retention time was 4.67 minutes. In addition, it was reported that paclitaxel must exhibit a UV absorbance ratio (227 nm/280 nm) of about 0.05 (Castor & Tyler 1993), and the paclitaxel standard was measured in this Example and, as a result, the UV absorbance ratio, A (280 nm)/A (227 nm), was 0.048.

Meanwhile, the cell line (sample) according to the present invention was analyzed by UPLC at absorbances of 227 nm and 280 nm. As a result, as shown in FIG. 22(b), the retention time was 4.70 minutes. In addition, the cell line (sample) extract was analyzed and, as a result, the UV absorbance ratio at 227 nm and 280 nm was A (280 nm)/A (227 nm)=1.24, suggesting that the cell line extract contained no paclitaxel.

In addition, the PDA spectrums of the paclitaxel standard and the cell line extract according to the present invention were analyzed. As shown in FIG. 22(c) and FIG. 22(d), the analysis results revealed that the cell line according to the present invention contained no paclitaxel.

Example 7

Preparation of Pharmaceutical Formulations

Formulation 1: Preparation of Tablet 100 mg of the cell line extract prepared in Example 1 was mixed with 100 mg of maize starch, 100 mg of lactose and 2 mg of magnesium stearate, and the mixture was compressed into a tablet according to a conventional tableting method.

Formulation 2: Preparation of Capsule Formulation 500 mg of the cell line extract prepared in Example 1 was filled in a soft gelatin capsule to prepare a capsule formulation.

Formulation 3: Preparation of Syrup Formulation 1 g of the cell line prepared in Example 1 was mixed with 10 g of isomerized sugar, 5 g of mannitol and a suitable amount of purified water, and the mixture was repared into 100 ml of a syrup formulation according to a conventional method.

Formulation 4: Preparation of Injection Solution 200 mg of the cell line extract prepared in Example 1 was heated and dissolved in 200 mg of physiological saline containing polyoxyethylene hydrogenated castor oil, thus preparing an injection solution containing the mixed extract at a concentration of 0.1%.

Example 8

Preparation of Functional Food: Preparation of Functional Beverage

Preparation 1: 200 mg of the cell line prepared in Example 1 was dissolved in 96 ml of water, and then 500 mg of vitamin C as a supplement, 1 g of each of citric acid and oligosaccharide as flavor enhancers and 0.05 g of sodium benzoate as a preservative were added thereto. Then, purified water was added thereto, thus preparing 100 ml of a functional beverage.

Preparation 2: 200 mg of the cell line extract prepared in Example 1 was dissolved in 96 ml of water, and then 500 mg of vitamin C as a supplement, 1 g of each of citric acid and oligosaccharide as flavor enhancers and 0.05 g of sodium benzoate as a preservative were added thereto. Then, purified water was added thereto, thus preparing 100 ml of a functional beverage.

INDUSTRIAL APPLICABILITY

As described above, a cell line according to the present invention and a lysate, extract and culture medium thereof are derived from a natural material, have minimized side effects compared to prior therapeutic drugs, are safe to the human body, are involved directly in the growth of cancer to induce cancer cell death, and show anticancer activity of inhibiting angiogenesis occurring in carcinogenesis. Accordingly, they are useful for the prevention, treatment and alleviation of cancer.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method for treating cancer, comprising administering any one or more selected from the group consisting of a cell line, a cell lysate, an extract of a cell line, and a culture of a cell line, wherein the cell line, the cell lysate, the extract of the cell line, and the culture medium of the cell line are all free of taxol, wherein said cell line is isolated from a cambium or procambium of *Taxus* and has the following characteristics:
   (a) being in an innately undifferentiated state without going through dedifferentiation and being not a callus; and
   (b) being a homogeneous cell line.

2. The method for treating cancer according to claim 1, wherein the cell line is additionally characterized in that: (a) it is present as single cells during suspension culture; (b) it has a growth rate higher than those of cell lines derived from tissues other than the cambium or procambium of *Taxus*; (c) it has low sensitivity to shear stress in a bioreactor compared to cell lines derived from tissues other than the cambium or procambium of *Taxus*; and (d) it has multiple vacuoles morphologically.

3. The method for treating cancer according to claim 1, wherein the cell line is obtained using an isolation method comprising the following steps of:
   (a) obtaining a *Taxus* cambium- or procambium-containing tissue;
   (b) inducing a cambium or procambium layer proliferated from the cambium or pro cambium and an amorphous callus layer proliferated from tissues other than the cambium or procambium by culturing the obtained *Taxus* cambium- or procambium-containing tissue; and
   (c) collecting a cell line from the cambium or procambium layer.

4. The method for treating cancer according to claim 3, wherein the step (c) is performed by proliferating cell line in a medium, which contains 3-5 wt % of mw sugar or sugar and at least one substance selected from the group consisting of methyl jasmonate, fungal extract, bacterial extract, yeast extract, chitosan, glucomanan, glucan, phenylalanine, benzoic acid, salicylic acid, arachonic acid, Staurosporine (STS), mevalonalonate N-benzolyglycine, Abscisic acid (ABA), Sodium nitroprusside (SNP), Isopentenylpyrophosphate (IPP), Butylated hydroxytoluene (BHT), 2-chloroethyl trimethylammonium chloride (CCC), ethephon, hippuic acid, ammonium ceric nitrate, $AgNO_3$, vanadyl sulfate, p-aminobenzoic acid, brassinosteroids, sodium alginate, and sodium acetate, and then collecting the cell line proliferated in the medium.

5. The method for treating cancer according to claim 1, wherein the extract is obtained using a solvent selected from the group consisting of distilled water, alcohol, acetone, DMSO (dimethyl sulfoxide), and mixed solvents thereof.

6. The method for treating cancer according to claim 1, wherein the cancer is selected from the group consisting of colon cancer, oral cavity carcinoma, lung cancer, prostate cancer, osteosarcoma, leukemia, uterine cancer, skin cancer, pancreatic cancer, breast cancer, gastric cancer, renal cancer and liver cancer.

7. The method for treating cancer according to claim 1, wherein the administering of the any one or more selected from the group consisting of a cell line, a lysate of a cell line, an extract of a cell line, and a culture of a cell line, wherein the cell line, the cell lysate, the extract of the cell line, and the culture medium of the cell line are all free of taxol, is done orally.

8. A method for improving a cancer patient condition, comprising orally administering food, wherein the food contains any one or more selected from the group consisting of a cell line, a lysate of a cell line, an extract of a cell line, and a culture of a cell line, wherein the cell line, the cell lysate, the extract of the cell line, and the culture medium of the cell line are all free of taxol, wherein said cell line is isolated from a cambium or pro cambium of *Taxus* and has the following characteristics:
  (a) being in an innately undifferentiated state without going through dedifferentiation and being not a callus; and
  (b) being a homogeneous cell line.

9. The method improving a cancer patient condition according to claim 8, wherein the cell line is additionally characterized in that: (a) it is present as single cells during suspension culture; (b) it has a growth rate higher than those of cell lines derived from tissues other than the cambium or procambium of *Taxus*; (c) it has low sensitivity to shear stress in a bioreactor compared to cell lines derived from tissues other than the cambium or procambium of *Taxus*; and (d) it has multiple vacuoles morphologically.

10. The method for improving a cancer patient condition according to claim 8, wherein the cell line is obtained using an isolation method comprising the following steps of
  (a) obtaining a *Taxus* cambium- or procambium-containing tissue;
  (b) inducing a cambium or procambium layer proliferated from the cambium or pro cambium and an amorphous callus layer proliferated from portions other than the cambium or pro cambium by culturing the obtained *Taxus* cambium- or procambium-containing tissue; and
  (c) collecting a cell line from the cambium or procambium layer.

* * * * *

UNITED STATES PATENT AND TRADEMARK OFFICE
CERTIFICATE OF CORRECTION

| | | |
|---|---|---|
| PATENT NO. | : 8,790,927 B2 | Page 1 of 1 |
| APPLICATION NO. | : 13/755517 | |
| DATED | : July 29, 2014 | |
| INVENTOR(S) | : Joong Hyun Park et al. | |

It is certified that error appears in the above-identified patent and that said Letters Patent is hereby corrected as shown below:

IN THE CLAIMS:

Column 18, Line 43: change "from the cambium or pro cambium and an amorphous" to --from the cambium or procambium and an amorphous--

Column 18, Line 51: change "a medium, which contains 3-5 wt % of mw sugar or sugar and" to --a medium, which contains 3-5 wt % of raw sugar or sugar and--

Column 18, Line 57: change "Sodium nitroprusside (SNP), Isopentenylpyrophosphate" to --Sodium nitroprusside (SNP), Isopentenyl pyrophosphate--

Column 19, Line 20: change "cambium or pro cambium of Taxus and has the following" to --cambium or procambium of Taxus and has the following--

Column 20, Line 14: change "isolation method comprising the following steps of" to --isolation method comprising the following steps of:--

Column 20, Line 18: change "from the cambium or pro cambium and an amorphous" to --from the cambium or procambium and an amorphous--

Column 20, Line 20: change "cambium or pro cambium by culturing the obtained" to --cambium or procambium by culturing the obtained--

Signed and Sealed this
Sixth Day of January, 2015

Michelle K. Lee
*Deputy Director of the United States Patent and Trademark Office*